United States Patent [19]

Orban et al.

[11] Patent Number: 4,536,593
[45] Date of Patent: Aug. 20, 1985

[54] PROCESS FOR THE PREPARATION OF STERICALLY HINDERED HYDROXPHENYLCARBOXYLIC ACID ESTERS

[75] Inventors: Ivan Orban; Eduard Troxler, both of Basel, Switzerland

[73] Assignee: Ciba-Geigy Corporation, Ardsley, N.Y.

[21] Appl. No.: 510,705

[22] Filed: Jul. 5, 1983

[30] Foreign Application Priority Data

Jul. 13, 1982 [CH] Switzerland .......................... 4264/82

[51] Int. Cl.$^3$ ...................... C07C 69/88; C07C 69/76
[52] U.S. Cl. ........................................ 560/75; 560/67
[58] Field of Search ..................... 560/67, 75

[56] References Cited

U.S. PATENT DOCUMENTS

| | | | |
|---|---|---|---|
| 3,330,859 | 7/1967 | Dexter et al. | 560/67 |
| 3,779,945 | 12/1973 | Dexter et al. | 560/67 |
| 4,417,071 | 11/1983 | Rosenberger | 560/67 |

FOREIGN PATENT DOCUMENTS

| | | |
|---|---|---|
| 2710630 | 9/1978 | Fed. Rep. of Germany . |
| 52-39646 | 3/1977 | Japan . |
| 6610810 | 2/1967 | Netherlands .......................... 560/67 |
| 1081789 | 8/1967 | United Kingdom . |

OTHER PUBLICATIONS

CA, 67, 89140q (1967).

Primary Examiner—Paul J. Killos
Attorney, Agent, or Firm—Luther A. R. Hall

[57] ABSTRACT

If the transesterification of esters of the formula

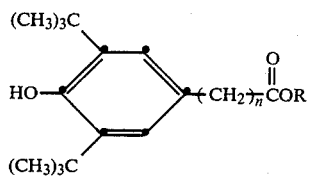

with alcohols of the formula III A—(OH)$_m$ is catalyzed by successive treatment with catalytic amounts (a) of a tin compound of a metal of the fourth main group or the fourth sub-group of the periodic system and (b) of an acid earth, compounds of the formula I

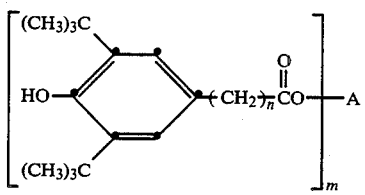

are obtained in virtually quantitative yield. The products thus obtained contain no troublesome by-products and do not have to be additionally purified.

R is methyl or ethyl, A is a radical derived from an m-hydric aliphatic alcohol, n is 0 to 2, and m is 1 to 4.

8 Claims, No Drawings

PROCESS FOR THE PREPARATION OF STERICALLY HINDERED HYDROXPHENYLCARBOXYLIC ACID ESTERS

The present invention relates to a process for the preparation of sterically hindered hydroxyphenylcarboxylic acid esters, in which the transesterification is catalysed by successive treatment with an organometallic compound and an acid earth.

Transesterification reactions for the preparation of sterically hindered hydroxyphenylcarboxylic acid esters are known. Thus, for example, German Auslegesschrift No. 1,201,349 and German Offenlegungsschrift No. 1,543,644 disclose transesterification reactions of this type in which alkali metal alcoholates are used as catalysts. According to German Offenlegungsschrift No. 2,150,327, transesterification reactions of the same type are catalysed by lithium amide. Varying minor amounts of by-products (usually oxidation products of 2,6-dialkylphenols) are formed in all these processes, and even very small amounts of these products cause a drastic reduction in the storage stability of the desired end product. The unavoidable removal of these by-products is very expensive in respect of time, labour and energy.

It has now been found that, surprisingly, transesterification with successive treatment with catalytic amounts of an organometallic compound of a metal of the fourth main group or the fourth sub-group of the periodic system and an acid earth leads to a virtually quantitative yield of pure end product, which does not have to be additionally purified since it contains no troublesome by-products.

The present invention accordingly relates to a process for the preparation of compounds of the formula I

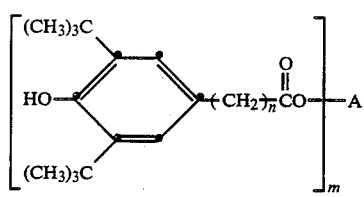

(I)

in which n is a number from 0 to 2, m is a number from 1 to 4 and A is a radical which has 2 to 18 carbon atoms and is derived from an m-hydric aliphatic alcohol, by transesterifying about m mols of an ester of the formula (II)

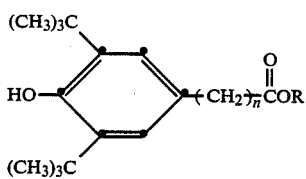

(II)

in which R is methyl or ethyl, with an alcohol of the formula (III)

   (III)

which comprises catalysing the transesterification by successive treatment with catalytic amounts of (a) an organometallic compound of a metal of the fourth main group or the fourth sub-group of the periodic system and (b) an acid earth.

A radical A derived from an m-hydric aliphatic alcohol is an m-valent substituted or unsubstituted aliphatic radical having 2 to 18 carbon atoms.

If m is 1, A is straight-chain or branched $C_2$-$C_{18}$-alkyl, for example ethyl, n-propyl, isopropyl, n-butyl, sec.-butyl, tert.-butyl, n-pentyl, n-hexyl, 2-ethylhexyl, n-octyl, 1,1,3,3-tetramethylbutyl, n-decyl, n-dodecyl, n-hexadecyl or n-octadecyl. n-Octadecyl is preferred.

If m is 2, A can be, for example, $C_2$-$C_{18}$-alkylene, preferably $C_2$-$C_6$-alkylene, such as dimethylene, trimethylene, tetramethylene, hexamethylene, 2,2-dimethyl-trimethylene, octamethylene, nonamethylene, decamethylene, dodecamethylene or octadecamethylene. The alkylene group can be interrupted by —O—, —S— or —N(R)—, as in 2-thiaprop-1,3-ylene, 3-thiapent-1,5-ylene, 4-oxaheptamethylene, 3,6-dioxaoctameth-1,8-ylene or 3,6-diazaoctameth-1,8-ylene. If A is interrupted $C_2$-$C_6$-alkylene, it is preferably a

group.

If m is 3, A can be a trivalent aliphatic $C_3H_5$- to $C_7H_{13}$-hydrocarbon radical, such as

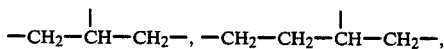

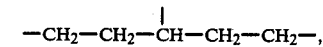

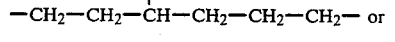

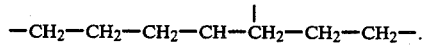

If m is 4, A can be a tetravalent aliphatic $C_4H_6$- to $C_{10}H_{18}$-hydrocarbon radical, such as

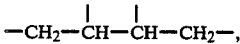

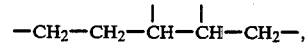

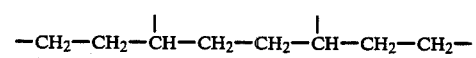

or, preferably, pentaerythrityl.

Examples of suitable organometallic compounds of a metal of the fourth main group or the fourth sub-group of the periodic system are compounds of the formula IV $(R_1O)_nM$ (IV)

in which $R_1$ is $C_1$–$C_{18}$-alkyl, phenyl or benzyl and M is the element Ge, Zr, Sn or, in particular, Ti, and, preferably, the compounds of the formula V

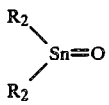
(V)

in which $R_2$ is $C_4$–$C_{18}$-alkyl.

A $C_4$–$C_{18}$-alkyl radical $R_2$ is, for example, n-butyl, sec.-butyl, tert.-butyl, n-pentyl, n-hexyl, n-octyl, 1,1,3,3-tetramethylbutyl, n-decyl, n-dodecyl, n-hexadecyl or n-octadecyl. A $C_1$–$C_{18}$-alkyl radical $R_1$ is also methyl, ethyl, n-propyl or isopropyl.

$R_1$ and $R_2$ are preferably n-butyl.

Examples of suitable acid earths are acid aluminium silicates, in particular aluminium hydrosilicates, for example zeolites and bentonites. Some of the aluminium can be replaced by iron or magnesium. Montmorillonite is preferred.

The starting substances are known. If some of them should be still novel, they can be prepared in a similar manner to known compounds.

The process according to the invention is particularly suitable for the preparation of compounds of the formula I by transesterification of an ester of the formula II with an alcohol of the formula III, in which formulae I, II and III n is the number 2, m is the number 1, 2 or 4, if m is 1, A is $C_2$–$C_{18}$-alkyl, if m is 2, A is $C_2$–$C_6$-alkylene or a

group, and, if m is 4, A is pentaerythrityl, and R is methyl.

The organometallic compound is advantageously employed in an amount of not less than 0.03% by weight, but preferably between 0.25 and 0.5% by weight, based on the ester of the formula II, at temperatures between 130° and 190° C., preferably between 150° and 175° C. The treatment with the organometallic compound lasts 2 to 5 hours.

The acid earth is advantageously employed in amounts of between 0.3 and 6% by weight, preferably between 1 and 5% by weight, based on the ester of the formula II, at temperatures between 50° and 150° C., preferably at 90° to 120° C. The treatment with the acid earth lasts from 15 minutes to 3 hours.

The preferred process according to the invention is the preparation of octadecyl 3-(3,5-di-tert.-butyl-4-hydroxyphenyl)-propionate by transesterification of methyl 3-(3,5-di-tert.-butyl-4-hydroxyphenyl)-propionate with octadecanol and successive treatment with (a) 0.25 to 0.5% by weight, based on the methyl 3-(3,5-di-tert.-butyl-4-hydroxyphenyl)-propionate, of dibutyl-tin oxide at temperatures between 150° and 175° C. and (b) 1 to 5% by weight, based on the methyl 3-(3,5-di-tert.-butyl-4-hydroxyphenyl)-propionate, of an aluminium hydrosilicate at temperatures between 90° and 120° C.

The transesterification can be carried out in vacuo and without a solvent or, preferably, under atmospheric pressure in the presence of an inert solvent, for example toluene or xylene. The amount of solvent depends on the desired reaction temperature. For example, at a reaction temperature of 170° C., addition of 40 to 50% by weight of toluene, based on the ester of the formula II, is particularly suitable. In order to achieve higher temperatures, the amount of solvent must be correspondingly reduced, and for lower temperatures it must be correspondingly increased.

The alcohol which forms in the transesterification reaction during the treatment with the organometallic compound is continuously distilled off during the reaction.

The suspension obtained after the treatment with the acid earth is clarified over a prewarmed Hyflo suction filter to remove the acid earth, the residue is evaporated, if necessary, and the melt is left to solidify. The solidified melt has only to be granulated by conventional methods in order to obtain the finished end product in a virtually pure form ready for its specific use.

The compounds of the formula I are useful stabilisers for organic materials which undergo decomposition, for example synthetic organic polymers, animal and vegetable oils, hydrocarbons, lubricants and the like.

The examples which follow illustrate the invention, without restricting it.

EXAMPLE 1

292.0 g (1.0 mol) of methyl 3-(3,5-di-tert.-butyl-4-hydroxyphenyl)-propionate, 275.4 g (1.02 mol) of stearyl alcohol and 130 g of toluene are introduced into a 1.5 liter flask, under nitrogen. The mixture is heated, and dehydrated azeotropically. It is cooled to 75° C. and 2.6 g of hydroquinone and 1.0 g (0.004 mol) of dibutyl-tin oxide are added. The mixture is now heated to 170° C., and methanol is thereby distilled off over a dephlegmator charged with warm water at 75° C. As soon as the internal temperature has reached 170° C., the dephlegmator is emptied, and distillation is continued at a constant internal temperature of 170° C. for a further 3 hours. The toluene thereby distilled off is replaced by a total of about 550 g of new toluene. The solution is cooled to 110° C.

10 g of Montmorillonit-Erde K-10 ® are added, the mixture is stirred at 107° to 110° C. for 30 minutes, the suspension is clarified over a Hyflo and the filtrate is evaporated in a rotary evaporator. The melt which remains is poured into a dish and seeded at about 50° C., and the crystal mass obtained after cooling is comminuted.

530 g (99.9% of theory) of octadecyl 3-(3,5-di-tert.-butyl-4-hydroxyphenyl)-propionate are obtained.

The end product contains about 0.1% of methyl 3-(3,5-di-tert.-butyl-4-hydroxyphenyl)-propionate.

EXAMPLE 2

292 g (1.0 mol) of methyl 3-(3,5-di-tert.-butyl-4-hydroxyphenyl)-propionate and 275.4 g (1.02 mols) of stearyl alcohol are introduced into a 1.5 liter flask, under nitrogen. The flask is evacuated, for dehydration, and the reaction mixture is stirred at 90° C. for 30 minutes. The flask is then let down with nitrogen and 1.0 g (0.004 mol) of di-butyl-tin oxide is added. The flask is evacuated and the melt is heated to 155° C. Most of the methanol formed in the reaction thereby distils off. A higher vacuum is now applied and stirring is continued at 155° C. for 5 hours. The mixture is cooled to 110° C., 10 g of Tonsil AC ® are added and the mixture is kept at 107° to 110° C. for 30 minutes. The suspension is clarified over a prewarmed Hyflo suction filter. The clarified melt is left to solidify and then comminuted.

525 g (99% of theory) of octadecyl 3-(3,5-di-tert.-butyl-4-hydroxyphenyl)-propionate are obtained.

The product contains about 1% of methyl 3-(3,5-di-tert.-butyl-4-hydroxyphenyl)-propionate.

What is claimed is:

1. A process for the preparation of a compound of formula I

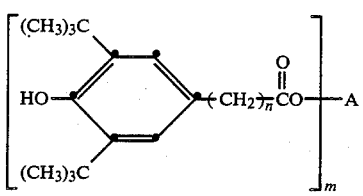

in which n is a number from 0 to 2, m is a number from 1 to 4 and A is a radical which has 2 to 18 carbon atoms and is derived from an m-hydric aliphatic alcohol, by transesterifying about m mols of an ester of formula (II)

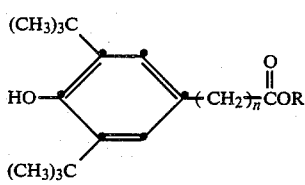

in which R is methyl or ethyl, with an alcohol of formula III $$A-OH)_m \qquad (III)$$

which comprises catalysing the transesterification by successive treatment under atmospheric pressure in the presence of an inert solvent with a catalytic amount of (a) a tin compound of formula V

in which $R_2$ is $C_4-C_{18}$-alkyl, and (b) an acid earth.

2. The process according to claim 1 for the preparation of a compound of the formula I by transesterifying an ester of the formula II with an alcohol of the formula III, wherein, in the formulae I, II and III, n is the number 2, m is the number 1, 2 or 4; when m is 1, A is $C_2-C_{18}$-alkyl; when m is 2, A is $C_2-C_6$-alkylene or a

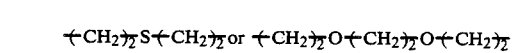

group, and; when m is 4, A is pentaerythrityl, and R is methyl.

3. The process according to claim 1, wherein an acid aluminium silicate is employed as the acid earth.

4. The process according to claim 1, wherein the tin compound is employed in an amount of not less than 0.03% by weight, based on the ester of the formula II.

5. The process according to claim 1, wherein the acid earth is employed in an amount of between 0.3 and 6% by weight, based on the ester of the formula II.

6. The process according to claim 1, wherein the treatment with the tin compound is carried out at a temperature between 130° and 190° C.

7. The process according to claim 1, wherein the treatment with the acid earth is carried out at a temperature between 50° and 150° C.

8. The process according to claim 1 for the preparation of octadecyl 3-(3,5-di-tert.-butyl-4-hydroxyphenyl)-propionate by transesterifying methyl 3-(3,5-di-tert.-butyl-4-hydroxyphenyl)-propionate with octadecanol, which comprises catalysing the transesterification by treatment with (a) 0.25 to 0.5% by weight, based on the methyl 3-(3,5-di-tert.-butyl-4-hydroxyphenyl)-propionate, of dibutyl-tin oxide at a temperature between 150° and 175° C. and (b) 1 to 5% by weight, based on the methyl 3-(3,5-di-tert.-butyl-4-hydroxyphenyl)-propionate of an aluminium hydrosilicate at a temperature between 90° and 120° C.

* * * * *